(12) United States Patent
Nishioka et al.

(10) Patent No.: US 6,177,405 B1
(45) Date of Patent: *Jan. 23, 2001

(54) CYCLIC ANALOGS OF TUFTSIN

(76) Inventors: Kenji Nishioka, 7820 Kendalia Dr., Houston, TX (US) 77036; John S. McMurray, 11031 Dunlap Dr., Houston, TX (US) 77096; B. Montgomery Pettitt, 5914 Birdwood, Houston, TX (US) 77074; Fahad Al-Obeidi, Hikma Pharmc. Co., P.O. Box 182400, Amman (JO)

( * ) Notice: Under 35 U.S.C. 154(b), the term of this patent shall be extended for 0 days.

This patent is subject to a terminal disclaimer.

(21) Appl. No.: 07/918,588

(22) Filed: Jul. 22, 1992

(51) Int. Cl.[7] ............................. A61K 38/12; C07K 7/64
(52) U.S. Cl. ................................ 514/11; 514/2; 530/317
(58) Field of Search ........................... 514/11, 2; 530/317

(56) References Cited

U.S. PATENT DOCUMENTS

| | | | | |
|---|---|---|---|---|
| 4,434,095 | * | 2/1984 | Chipens | 530/317 |
| 4,720,484 | * | 1/1988 | Vincent | 514/18 |
| 4,816,449 | * | 3/1989 | Hahn | 514/17 |
| 4,874,850 | * | 10/1989 | Paradies | 514/3 |
| 4,965,250 | * | 10/1990 | Vincent | 518/18 |
| 4,994,554 | * | 2/1991 | Audhya | 530/327 |
| 5,026,909 | * | 6/1991 | Zolotarev | 562/575 |
| 5,028,593 | * | 7/1991 | Nishioka | 514/18 |
| 5,045,530 | * | 9/1991 | Paradies | 514/9 |
| 5,057,518 | * | 10/1991 | Paradies | 514/274 |

FOREIGN PATENT DOCUMENTS

| | | | |
|---|---|---|---|
| 0325 044 | * | 7/1989 | (EP) . |
| 2 058 085 | * | 4/1981 | (GB) . |
| WO 86/01211 | * | 2/1986 | (WO) . |

OTHER PUBLICATIONS

Chipens, "Elongated and Cyclic Analogues of Tuftsin and Rigin," Proc. Eur. Pept. Symp. 16th, pp. 445–450 (1981).*

Chipens et al., "Cyclic Analogs of Linear Peptides," Proc. Am. Pept. Symp. 6th, pp. 567–570 (1979).*

Kataev et al., "CD Spectrum and Conformational Distribution of Cyclotuftsin in Solution," FEBS, 190 (2):214–216 (Oct. 1985).*

Nikiforovich et al., "Biologically Active Conformation of Tuftsin," Int. J. Peptide Protein Res., 23:271–275 (1984).*

Nikiforovich et al., "Conformational Calculations and Biologically Active Conformations of Cyclopeptides," Proc. Eur. Pept. Symp. 17th, pp. 735–739 (1983).*

Nishioka et al., "A Comparative Study of [LEU[1]]Tuftsin and Tuftsin, A Natural Phagocytosis–Stimulating Peptide," Int. J. Biochem., 23:627–630 (1991).*

Metcalf, "The Granulocyte–Macrophage Colony–Stimulating Factors," Science, 229:16–22 (Jul. 5, 1985).*

Stabinsky et al., "The Phagocytosis Stimulating Peptide Tuftsin: Further Look Into Structure–Function Relationships," Mol. Cell. Biochem., 30:165–170 (1980).*

Fridkin et al., "Tuftsin, Thr–Lys–Pro–Arg, Anatomy of an Immunologically Active Peptide," Mol. Cell. Biochem., 41:73–97 (1981).*

Siemion et al., "Tuftsin Analogs and Their Biological Activity," Mol. Cell. Biochem., 41:99–112 (1981).*

Delange et al., "Leucine Aminopeptidase and Other N–Terminal Exopeptidases," The Enzymes, P.D. Boyer (Editor), vol. III, pp. 81–118 (1971).*

O'Connor et al., "Quenched Molecular Dynamics Simulations of Tuftsin and Proposed Cyclic Analogues," (In Press).*

Singh et al, Experientia, 48, pp. 994–996, (1992).*

Corron et al, J. Reed. Chem., 35, pp. 2870–2881, (1992).*

Berthier et al, Chemical Pharmacology, vol. 41, (10), pp. 1411–1418, (1991).*

* cited by examiner

*Primary Examiner*—Keith D. MacMillan
*Assistant Examiner*—T. D. Wessendorf

(57) ABSTRACT

The useful cyclic peptides cyclo[Thr-Lys-Pro-Arg-Gly] and cyclo[Thr-Lys-Pro-Arg-Asp] are disclosed.

6 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 5 amino acids
        (B) TYPE: amino acid
        (D) TOPOLOGY: circular (xi) SEQUENCE DESCRIPTION: SEQ ID NO:1:

Thr Lys Pro Arg Gly
1           5

(2) INFORMATION FOR SEQ ID NO:2:

(i) SEQUENCE CHARACTERISTICS:
        (A) LENGTH: 5 amino acids
        (B) TYPE: amino acid
        (D) TOPOLOGY: circular (xi) SEQUENCE DESCRIPTION: SEQ ID NO:2:

Thr Lys Pro Arg Asp
1           5

CYCLIC ANALOGS OF TUFTSIN

The Government has certain rights in this invention pursuant to National Institutes of Health Grant nos. GM 37657 and CA 53617.

BACKGROUND OF THE INVENTION

The present invention relates to peptides with useful biological activity, and more specifically, to analogs of the peptide tuftsin, Thr-Lys-Pro-Arg (TKPR).

A variety of factors are involved in vivo in the modulation of the immunological system, and also in the growth and differentiation of normal and tumor cells. Tuftsin is one such factor. Tuftsin, which is located between residues 289 and 292 of the heavy chain of leukokinin (a leukophilic IgG), has been found to have a number of interesting biological activities, such as antitumor, anti-infection, anti-AIDS, and growth factor activities, and enhancement of the phagocytic and cytotoxic activities of leukocytes.

Without wishing to be bound to any particular theory of activity, it is presently believed that tuftsin is released through a process in which the carboxyl-terminus of tuftsin in the Fc portion of the leukophilic IgG is cleaved from the adjacent part of the molecule by a splenic enzyme, tuftsin endocarboxypeptidase. Tuftsin with the exposed carboxyl terminus is then transported as an integral part of the leukophilic IgG to target cells, polymorphonuclear leukocytes (PMNs). The leukokinin molecule binds to the Fc receptor on the membrane of the PMN. There tuftsin is cleaved at the $NH_2$-terminus from the Fc portion of the heavy chain of the leukokinin by a specific trypsin-like protease (leukokininase) on the membrane of the target cells. Tuftsin thus released binds to a specific PMN membrane receptor resulting in stimulation of phagocytosis. Tuftsin is now also known to bind monocyte-macrophages and natural killer (NK) cells and modulate their cellular functions.

The physiological importance of tuftsin has been demonstrated in patients with congenital familial tuftsin abnormality; many such individuals produce a peptide which competes with tuftsin, and are more susceptible to infection than are normal subjects. Similar susceptibility to infection can be observed in splenectomized hosts, presumably due to loss of the spleen enzyme, tuftsin endocarboxypeptidase. Tuftsin deficiency has also been found among patients with sickle cell disease, AIDS, AIDS-related complex, acute granulocytic leukemia, myelofibrosis, and idiopathic thrombocytopenic purpura, all of whom also exhibit increased susceptibility to infection.

Researchers have attempted to find analogs of tuftsin which possess improved activity in one or more respects. However, most of the analogs synthesized either have not possessed the desired activity, or have been found to be competitive inhibitors of tuftsin. Therefore, a need exists for peptides which have advantages in biological activity or in other respects over tuftsin.

SUMMARY OF THE INVENTION

The present invention relates to a biologically active peptide selected from the group consisting of cyclo[Thr-Lys-Pro-Arg-Gly] (SEQ ID no. 1)and pharmaceutically acceptable salts thereof, and cyclo[Thr-Lys-Pro-Arg-Asp] (SEQ ID no. 2) and pharmaceutically acceptable salts thereof. The present invention also relates to a therapeutic composition which comprises a pharmaceutically acceptable carrier and at least one of the above peptides.

The above cyclic tuftsin analogs are believed, based on studies performed using high temperature quenched molecular dynamics modeling, to adopt aspects of the conformational distribution in solution similar to that of linear tuftsin. This and the advantage of cyclization are believed to aid in the binding of these analogs to tuftsin-specific receptor sites, and thus to result in biological activity similar to that of tuftsin.

The peptides of the present invention should be useful as immunoaugmenting agents with growth factor activity, including use for prophylaxis and treatment of cancer and infections such as AIDS, infections related to sickle-cell disease, splenectomy, ambulatory peritoneal dialysis, therapy-induced immune suppression, lupus erythematosus, trauma, and idiopathic thrombocytopenic purpura, and tuftsin abnormality disease.

The peptides of the present invention have the particular advantage of greater potency than tuftsin itself. In addition, they retain useful activity when administered orally, due to their resistance to enzymatic degradation.

DETAILED DESCRIPTION OF SPECIFIC EMBODIMENTS

Figure 1:
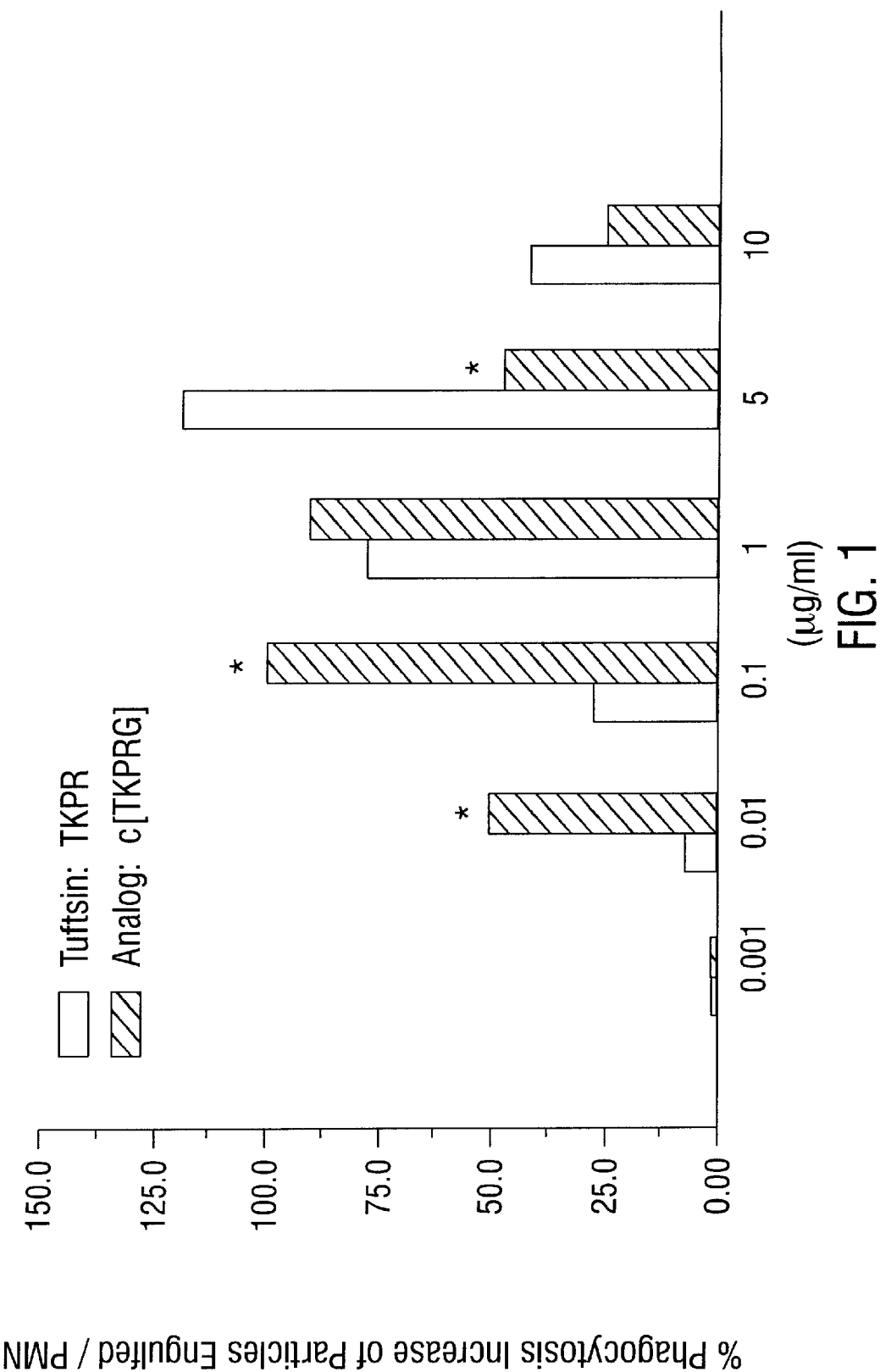
FIG. 1 shows the results of a phagocytosis dose-response assay using tuftsin and the cyclic analog cyclo[Thr-Lys-Pro-Arg-Gly] (SEQ ID no. 1) (c[TKPRG]). * indicates a statistically significant difference from tuftsin by Student t-test.

Flexible biological molecules, such as the linear peptide tuftsin, probably exist in numerous low-energy states in solution, and a particular, active conformation may only be obtained upon interaction with a specific receptor. Therefore, the conformational properties of certain tuftsin analogs in solution were studied in an attempt to determine which analogs could possess useful activity. Analysis performed used quenched molecular dynamics indicated that cyclo[Thr-Lys-Pro-Arg] and cyclo[Thr-Lys-Pro-Arg-Lys] would have substantial conformational differences from linear tuftsin in solution, and therefore would likely have little or no biological activity. However, such analysis indicated that cyclo[Thr-Lys-Pro-Arg-Gly] (SEQ ID no. 1) and cyclo[Thr-Lys-Pro-Arg-Asp] (SEQ ID no. 2)displayed conformational properties in solution similar to those of linear tuftsin, and therefore were candidates for synthesis and biological testing.

Preparation of cyclo [Thr-Lys-Pro-Arg-Gly] (SEQ ID no. 1)

This synthesis is similar to a method disclosed in Wooton and Watts (1989). The amino acids were protected on the α-amino group with the 9-fluorenylmethoxycarbonyl (Fmoc) group (Atherton and Sheppard, 1989; Fields and Noble, 1990). The side chains of the amino acids were protected with the following groups: threonine, t-butyl ether; lysine, t-butyloxycarbonyl (Boc); and arginine, 4-methoxy-2,3,5-trimethylbenzenesulfonyl (Mtr) (Atherton et al, 1983).

To 1 gm of aminomethylated polystyrene (nominal loading, 0.7 mmole/gm), a solution of 0.823 gm of 4-hydroxymethyl-3-methoxyphenoxyacetic acid (4.2 mmole) (Atherton et al, 1981a) and 0.656 mL of diisopropyl carbodiimide (DIPCDI, 4.2 mmole) in 6 mL of $CH_2Cl_2$ plus enough dimethylformamide (DMF) to effect solution was added. After 45 minutes the resin was drained and washed. The resin was acylated with 4.2 mmole of the symmetric anhydride of Fmoc-glycine in 15 mL of DMF using 0.085 gm of 4-dimethylaminopyridine (DMAP) as a catalyst. After 45 min the resin was washed and drained. The acylation was repeated. The remaining Fmoc amino acids were added in 3-fold molar excess and were activated with equimolar amounts of DIPCDI and 1-hydroxybenzotriazole (HOBt). The solvent for couplings and washes was $DMF/CH_2Cl_2$ (1:1). Fmoc removal was accomplished by treating the resin 2 times (2×) with 20% piperidine in DMF. On completion of the assembly, the amino terminal Fmoc group was left intact, and the peptide was cleaved from the resin by passing 100 mL of 1% trifluoroacetic acid (TFA) in $CH_2Cl_2$ through the resin in 30 minutes. The eluant drained into 5 mL of ice cold DMF. The solvents were evaporated to ca 5 mL and the peptide was isolated by dropping the solution into 30 mL of ice cold $H_2O$ and collecting the precipitate on a filter. After drying overnight in high vacuum over $P_2O_5$, the yield was 0.350 gm, 0.31 mmole. To 0.140 gm of this peptide, was added 10% diethylamine in DMF. This reaction stirred for 2 hours at which time the solvents were removed by evaporation in vacuo and the residue was washed with diethylether ($Et_2O$). The residue was dissolved in 7.5 mL of DMF and was added over 8 hours to a solution of 81 µL of diphenylphosphoryl azide (DPPA, 0.38 mmole) and 21 µL of triethylamine (0.30 mmole) in 90 mL of DMF kept at −5° C. The reaction was allowed to warm up to room temperature, and 14 hours later the solvents were evaporated off in vacuo. The residue was dissolved in 75 mL of ethylacetate (EtOAc) and was washed with 5% $KHSO_4$, 5% $NaHCO_3$, and brine. The solvent was removed in vacuo yielding 150 mg of a crystalline solid. This was purified by silica gel chromatography using a gradient of methanol in chloroform to yield 42 mg of product. The residue was treated with TFA/phenol 95:5 for 5 hours. The TFA was removed in vacuo. The residue was dissolved in water, extracted with $Et_2O$, and was lyophilized. The product was purified to homogeneity by reversed phase HPLC using a gradient of acetonitrile in water containing 0.1% heptafluorobutyric acid. Yield 20 mg. FAB-MS (M+H) calc'd., 540.3; found 540.4. Amino acid analysis: Thr, 1.11; Lys, 1.00, Pro, 0.95; Arg, 1.01; Gly, 1.20.

Preparation of 4-hydroxymethylphenoxyacetyl-leucyl-aminomethylated polystyrene (ALH-resin)

Aminomethylated polystyrene resin (3 gm, loading: 0.3 mmole/gm, 0.9 mmole) was derivatized with Fmoc-leucine by adding 4 equivalents each of the amino acid derivative, HOBt, and DIPCDI in 8 mL of $DMF/CH_2Cl_2$ (1:1). After overnight reaction the reagents were washed out of the resin, and the resin was capped with 15 equivalents of acetic anhydride. The reagents were washed out, and the Fmoc group was removed with 20% piperidine in DMF, 1×3 minutes plus 1×7 minutes. The reagents were washed out of the resin. 4-Hydroxymethylphenoxyacetic acid (Atherton et al., 1981b) (4 equivalents) was dissolved in 10 mL of $DMF/CH_2Cl_2$ (1:1), activated with 4 equivalents of DIPCDI and this solution was added to the Leu-resin. At 30 minutes into the reaction 5 mL of additional solvent was added. After 5 hours the reagents were washed from the resin. The resin was then washed with $Et_2O$, dried in vacuo and stored.

Preparation of cyclo[Thr-Lys-Pro-Arg-Asp] (SEQ ID no. 1)

The amino acids used in this synthesis were protected on the α-amino group with the Fmoc group. The side chains of the amino acids were protected with the following groups: threonine, t-butyl ether; lysine, Boc; and arginine, Mtr. The symmetric anhydride of the α-2,4-dimethoxybenzyl ester of Fmoc-aspartic acid (Fmoc-Asp-ODmb, McMurray, 1991) was prepared by dissolving 0.44 gm (0.87 mmole) of Fmoc-Asp-ODmb in 10 mL of $CH_2Cl_2$, adding 68 µL (0.44 mmole) of DIPCDI, stirring for 20 minutes, and evaporating the solvent. The symmetric anhydride was dissolved in 3 mL of DMF and added to the ALH-resin (1.0 gm, 0.30 mmole). The acylation was catalyzed by the addition of 36.6 mg of DMAP(0.3 mmole) in 0.5 mL of DMF. After one hour the resin was drained, and washed with $DMF/CH_2Cl_2$ (1:1). One half of the Fmoc- Asp-ODmb resin was used in the following synthesis. The remaining amino acids were added in 4 fold excess by dissolving in 3 mL of $DMF/CH_2Cl_2$(1:1), activating by adding equimolar amounts of DIPCDI and HOBt, and adding this solution to the resin. After one hour the reagents were washed from the resin, and the Fmoc group was removed by treating the peptidyl resin with 20% piperidine in DMF, 1×3 minutes plus 1×7 minutes. When the sequence was assembled the amino terminal Fmoc group was not removed. The resin was washed 5× with $CH_2Cl_2$ and then with 5×15 mL of $CH_2Cl_2$ containing 1% TFA for 5 minutes each. After washing with $CH_2Cl_2$ 3× then $DMF/CH_2Cl_2$ (1:1) 3×, the Fmoc group was removed as above. DIPCDI, 94 µL, and 92 mg of HOBt in 3 mL of DMF were added to the resin. After 2 days the resin was drained, washed with $DMF/CH_2Cl_2$ (1:1), $CH_2Cl_2$ and $Et_2O$, and was dried. Yield: 0.626 mg. The resin, 0.597 gm, was treated with TFA/phenol (95:5) overnight, filtered, and washed with TFA. The combined filtrate and washings were evaporated in vacuo to ca 5 mL. This was dropped into 30 mL of ice cold ether. The peptide was collected by centrifugation, and the pellet was suspended in ether and centrifuged 2× more. The pellet was dried in high vacuum over $P_2O_5$ and NaOH overnight to yield 92 mg of a white powder. The residue was purified by Sephadex G-25 chromatography using 0.1 M acetic acid as the eluant to yield 5.3 mg of a white solid. FAB MS calc'd, 598.2; found 598.3.

Alternative methods of synthesis

These peptides could by synthesized by any of a variety of methods using any number of protecting groups for the N-terminal amino group, C-terminal carboxyl group, and side chain hydroxyl, amino and guanidino groups of the amino acids. It would be required that the amino and carboxyl terminal protecting groups be removed under conditions that would leave the side chain protecting groups intact. Linear precursors could be synthesized using either solution phase or solid phase methods. Cyclization of linear peptides prepared in solution, or on solid phase and isolated from the insoluble support, could be carried out using any method capable of forming amide bonds including forming C-terminal active esters and activating the C-terminus with coupling reagents such as carbodiimides, DPPA, benzotriazole-1-yl-oxy-tris-(dimethylamino)phosphonium hexafluorophospate (BOP), benzotriazole-1-yl-oxy-tris-pyrrolidino-phosphonium hexafluorophosphate (PyBOP), bromo-tris-pyrrolidino-phosphonium hexafluorophosphate (PyBrOP), 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU). Alternatively peptides could be cyclized using solid phase techniques such as that described for cyclo[Thr-Lys-Pro-Arg-Asp] or by using the oxime resin as described by Osapay et al. (1990).

SYNTHESIS REFERENCES

1. Atherton E.; Brown, E.; Priestly, G.; Sheppard, R. C. (1981a) Proc. 7th Am. Peptide Symp.; Rich, D. H. and Gross, E., Eds; Peirce Chemical Co., Rockford Ill; pp 163–175
2. Atherton E.; Logan, C. J.; Sheppard, R. C. (1981b) *J. Chem. Soc. Perkin* I 538–546
3. Atherton E.; Sheppard, R. C.; Wade, J. D. (1983) *J. Chem. Soc. Comm.* 1060–1062

4. Atherton, E.; Sheppard, R. C. (1989) *Solid Phase Peptide Synthesis: A Practical Approach* Oxford University Press, Oxford
5. Fields, G. B.; Noble, R. L. (1990) *Int. J. Peptide Protein Res.* 35, 161–214
6. McMurray, J. S. (1991) *Tetrahedron Letters* 32, 7679–7682
7. Osapay, G.; Profit, A.; Taylor, J. W. (1991) *Tetrahedron Letters* 43, 2161–2164
8. Wooton, G.; Watts, E. A. (1989) EP 0 325 044 A2

Cyclo[Thr-Lys-Pro-Arg-Gly] (SEQ ID no. 1) was further purified by reversed-phase HPLC (C-18 column) using 0.25 M ammonium acetate buffer, pH 4.7 and lyophilized. The chemical synthesis and purification procedures of tuftsin were as described in U.S. Pat. No. 5,028,593, which is incorporated here by reference. Endotoxin contents of purified peptides are routinely examined by the Whittaker Quantitative Chromogenic LAL, QCL-100 kit and are less than 0.1 Endotoxin Unit per ml.

Bioassays were performed using the procedures described below.

Phagocytosis Assay

Human polymorphonuclear leukocytes (PMNs) were prepared from venous blood of healthy donors. Heparinized blood was mixed with dextran and kept at 37° C. for 1 hour. The leukocyte-rich plasma was collected and centrifuged. The resulting pellet was washed with Hank's balanced salt solution (HBSS). The pellet was then suspended into HBSS, layered over Lymphocyte Separation Medium (LSM) and centrifuged. The sedimented cells were washed with HBSS. Contaminant erythrocytes were lysed by suspending the cells in sterile water for 15 seconds. The isotonicity was then restored by adding 10× HBSS. After centrifuging, the PMNs were washed with HBSS, suspended in the same medium, counted, and adjusted to $1 \times 10^6$ viable cells/ml (viability>95% by trypan blue dye exclusion). Cells (0.5× $10^6$/well) were plated in 24 well plate and placed in a 37° C. $CO_2$ incubator for 30 min to form a monolayer. Thereafter the supernatant was aspirated. Tuftsin or analog in 250 $\mu$l HBSS and $2.5 \times 10^7$ fluorescent microspheres (2 $\mu$m diameter) in 250 $\mu$l HBSS, were added to each well resulting in a particle to PMN ratio of 50:1, mixed, and incubated for 15 min. The supernatant was then quickly aspirated and each well washed with HBSS. One ml of trypsin (0.25% in saline) was added to each well and the plate incubated for 15 min to detach the cells and remove non-engulfed particles associated on the surface of PMN. The cells were transferred, layered over 2 ml fetal bovine serum (FBS), and centrifuged. The supernatant containing free particles were removed. The cell pellet was suspended, fixed in 2% paraformaldehyde, and plated again into a well. After 10 min, particles engulfed per PMN were counted under a microscope (100 cells per well). The mean values from triplicates were used to calculate percent phagocytosis increase over control mean value.

Thymidine Incorporation Assay

THP-1 (a human acute monocytic leukemia line) cells were subcultured in RPMI-1640 medium with 10% FBS. Next day THP-1 cells were collected, washed with RPMI-1640 medium with 2% FBS, and plated into well with peptide ($1 \times 10^6$ cell in 1 ml). The plate was incubated for 18 hours. $^3$H-thymidine (0.1 $\mu$Ci per well) was then introduced. The plate was incubated for another hour. The cells were collected into a tube using 1 ml of cold HBSS. After washing the cells twice, the cells were mixed with 0.2 ml of 0.1% sodium dodecyl sulfate, and transferred to a liquid scintillation vial for determination of radioactivity. The mean values from triplicates were used to calculate percent increase over control mean value.

Tumor Cell Cytotoxicity Assay by Human NK Cells

Heparinized blood was layered over Leukoprep tube (30 ml per tube), and centrifuged. The mononuclear cells at interphase were collected, washed with HBSS, suspended in RPMI-1640 medium with 10% FBS (15 ml per 30 ml starting blood), plated on Petri dishes, and incubated for 1 hour. Non-adherent cells were collected, suspended in RPMI-1640 medium with 5% FBS, and adjusted to $1 \times 10^6$/ml for 4 hour $^{51}$Cr release assay. The viability of this NK cell enriched fraction was assessed with trypan blue.

The tumor target cells, K-562, were harvested from culture, washed with RPMI-1640 medium with 5% FBS, and centrifuged. Pelleted cells of $2 \times 10^6$ K-562 were suspended into 0.2 ml of 100 $\mu$Ci of $^{51}$CrO$_4$ in saline, and labelled for 90 min in the incubator. The labelled target cells were washed with RPMI-1640 medium with 5% FBS, suspended in the same medium, and adjusted to a suspension of $2 \times 10^5$/ml. These cells were plated to each well ($1 \times 10^4$ cells/0.05 ml) of a 96-well round-bottom microtiter plate. A portion of NK cell-enriched fraction was activated for 1 hour at 37° C. in the presence of peptide in RPMI-1640 medium with 5% FBS, and washed with RPMI medium. After adding appropriate numbers of these activated cells to each well (final volume: 0.2 ml), a plate was centrifuged for 5 min, and incubated for 4 hours. The plate was removed and centrifuged. Supernatants were absorbed into filter strips and collected using the Skatron Supernatant Collection System (Flow Labs, Inc., McLean, Va.). Filters containing radioactive supernatants were counted on a γ counter, and counts per minutes (cpm) were recorded. Percent cytotoxicity (% specific lysis) was calculated by the following formula:

$$\text{Experimental cpm} - \text{Spontaneous cpm} \times 100\ \text{Maximum cpm} - \text{Spontaneous cpm}$$

Spontaneous cpm was obtained by incubating the tumor target cells alone in the medium. Maximum cpm was obtained by releasing the radioactivity from the target cells by treatment with Triton X-100. The mean values from triplicates were used to calculate percent increase in cytotoxicity over control mean value.

Using purified cyclo[Thr-Lys-Pro-Arg-Gly] (SEQ ID no. 1) as an example, we have examined in vitro biological activities of this peptide. A phagocytosis assay was performed to compare the activity of cyclo[Thr-Lys-Pro-Arg-Gly] (SEQ ID no. 1) to that of tuftsin. The optimum concentration of tuftsin in this assay is 5 $\mu$g/ml. However, the optimum concentration for cyclo[Thr-Lys-Pro-Arg-Gly] (SEQ ID no. 1) (c[TKPRG])was found to be 0.1 $\mu$g/ml, 50 fold lower than tuftsin, as shown in FIG. 1, indicating its significantly superior potency over tuftsin at lower concentrations of 0.01 and 0.1 $\mu$g/ml. There was no significant difference in the extent of phagocytosis at 5 $\mu$g/ml of tuftsin and at 0.1 $\mu$g/ml of cyclo[Thr-Lys-Pro-Arg-Gly] (SEQ ID no. 1).

Figure 2:
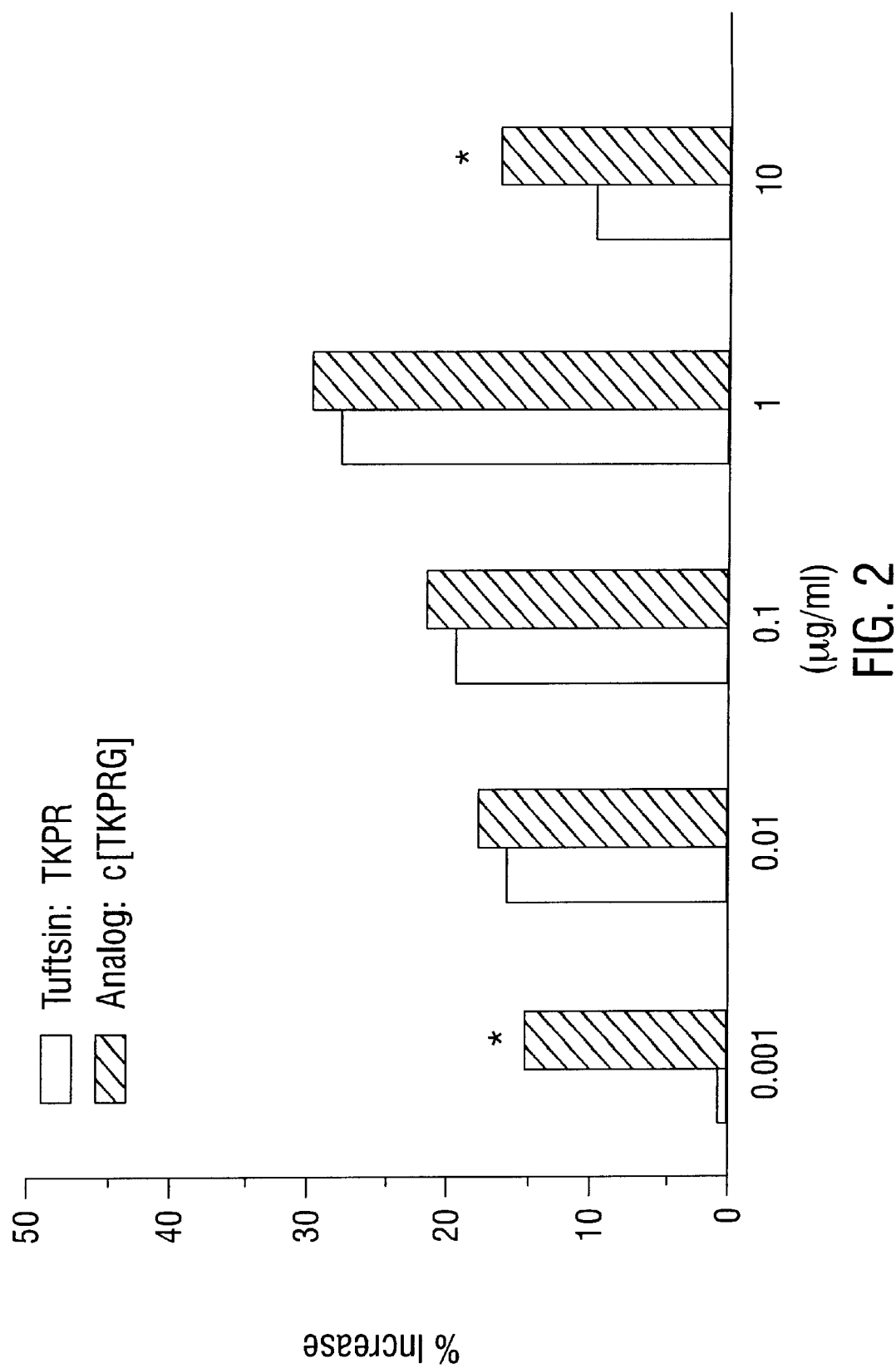
FIG. 2 shows the results of a thymidine incorporation assay (growth stimulation effect) using the same substances.

To examine the growth stimulating effect of peptides, a thymidine incorporation experiment was performed using THP-1 (human acute monocytic leukemia) cell line. As shown in FIG. 2, cyclo[Thr-Lys-Pro-Arg-Gly] (SEQ ID no. 1) displayed significantly greater activities than tuftsin at 0.001 and 10 µg/ml.

Figure 3:
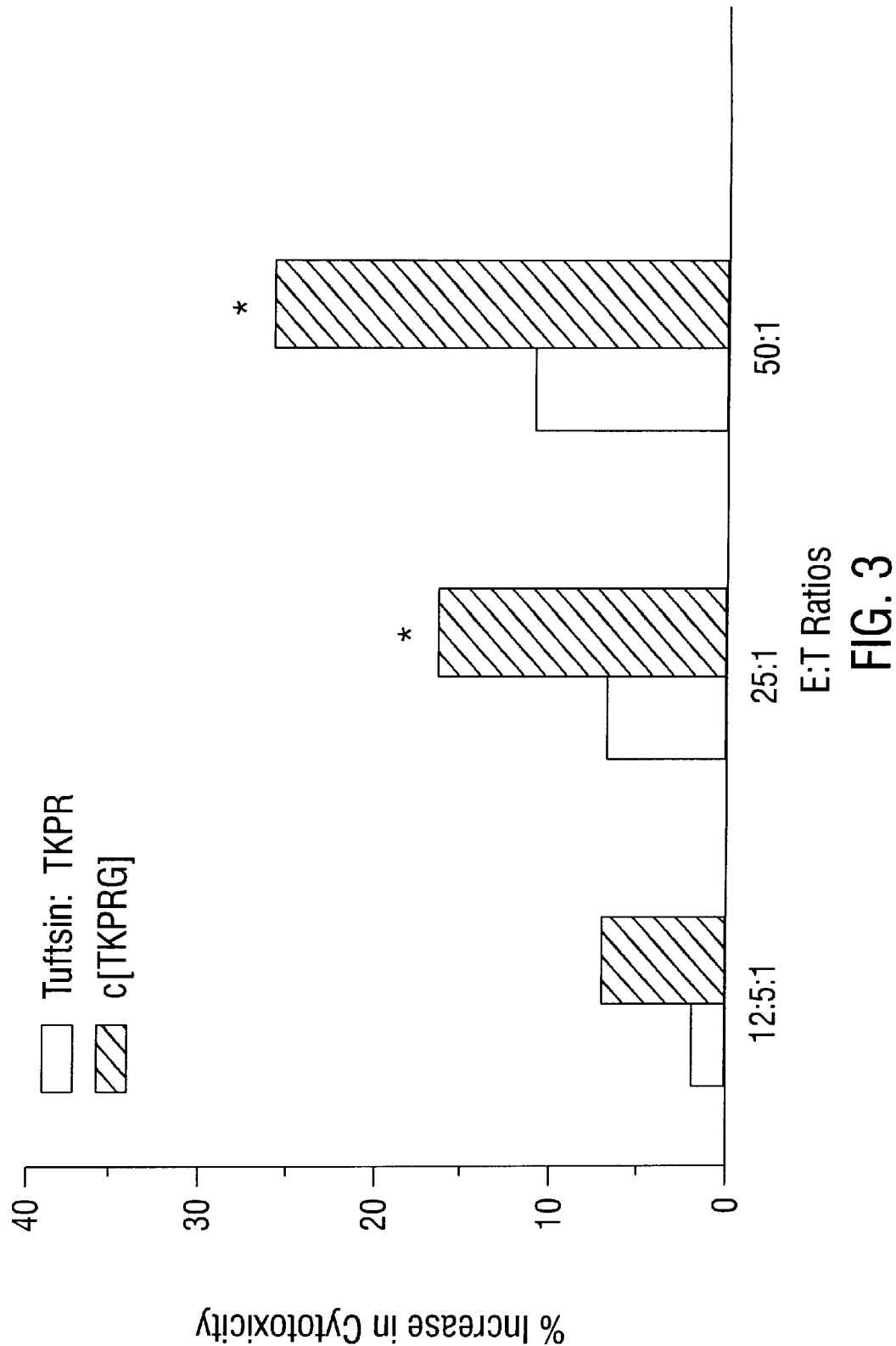
FIG. 3 shows the results of a human NK cell tumor cell cytotoxicity assay of the same substances.

To examine tumor cell cytotoxicity enhancement of human NK cells by this peptide, we then performed a human NK cytotoxicity assay. As shown in FIG. 3, the cyclic peptide showed significantly greater cytotoxicity at effector:target ratios of 25:1 and 50:1 at peptide concentration of 1 µg/ml.

The cyclic derivatives of the present invention are believed to be resistant to degradation by the ecto-enzyme leucine aminopeptidase located on the surface of PMNs. This may be one of the causes of their high potency as compared to tuftsin itself, which is inactivated when its N-terminal amino acid, threonine, is cleaved by this enzyme. Also, because tuftsin has been found to have some antitumor activity when administered orally, the cyclic analogs of the present invention are believed to have even greater activity by the oral route of administration, due to their increased resistance to enzymatic degradation.

The peptides of the present invention can be administered to a mammalian subject in the form of a pharmaceutical composition. This can take the form of a solution which contains a pharmaceutically acceptable carrier, for example a sterile isotonic aqueous solution. The composition can be employed in admixture with pharmaceutically acceptable excipients which do not deleteriously react with the active peptides.

The mode of administration can be parenteral, i.e., by intravenous, intraarterial, intramuscular, intralymphatic, intraperitoneal, subcutaneous, intrapleural, or intrathecal injection or infusion. The administration could also be through oral dosage, or by inhalation or topical application. A pharmaceutically effective amount will be administered, preferably in a dosage between about 1 µg and about 100 mg per m$^2$.

The preceding description is intended to provide examples of specific embodiments of the present invention, not to provide an exhaustive list of all possible embodiments of the present invention. Persons skilled in this field will recognize that modifications could be made to the specific embodiments described above which would remain within the scope of the present invention.

We claim:

1. A peptide selected from the group consisting of:
    cycl[Thr-Lys-Pro-Arg-Gly] (SEQ ID no. 1) and pharmaceutically acceptable salts thereof; and
    cyclo[Thr-Lys-Pro-Arg-Asp] (SEQ ID no. 2) and pharmaceutically acceptable salts thereof.

2. Cyclo[Thr-Lys-Pro-Arg-Gly] (SEQ ID no. 1) and pharmaceutically acceptable salts thereof.

3. Cyclo[Thr-Lys-Pro-Arg-Asp] (SEQ ID no. 2) and pharmaceutically acceptable salts thereof.

4. A therapeutic composition, comprising a pharmaceutically acceptable carrier and a peptide selected from the group consisting of:
    cyclo[Thr-Lys-Pro-Arg-Gly] (SEQ ID no. 1) and pharmaceutically acceptable salts thereof; and
    cyclo[Thr-Lys-Pro-Arg-Asp] (SEQ ID no. 2) and pharmaceutically acceptable salts thereof.

5. A therapeutic composition, comprising a pharmaceutically acceptable carrier and cyclo[Thr-Lys-Pro-Arg-Gly] (SEQ ID no. 1) or a pharmaceutically acceptable salt thereof.

6. A therapeutic composition, comprising a pharmaceutically acceptable carrier and cyclo[Thr-Lys-Pro-Arg-Asp] (SEQ ID no. 2) or a pharmaceutically acceptable salt thereof.

\* \* \* \* \*

UNITED STATES PATENT AND TRADEMARK OFFICE
CERTIFICATE OF CORRECTION

PATENT NO.   : 6,177,405 B1                                                       Page 1 of 1
DATED        : January 23, 2001
INVENTOR(S)  : Kenji Nishioka, John S. McMurray, B. Montgomery Pettitt and Fahad Al-Obeidi It is certified that error appears in the above-identified patent and that said Letters Patent is hereby corrected as shown below:

Column 8,
Line 4, delete "cycl" and insert -- cyclo --

Signed and Sealed this

Sixteenth Day of October, 2001

Attest:

NICHOLAS P. GODICI
Attesting Officer    Acting Director of the United States Patent and Trademark Office

UNITED STATES PATENT AND TRADEMARK OFFICE
CERTIFICATE OF CORRECTION

PATENT NO.   : 6,177,405 B1
DATED        : January 23, 2001
INVENTOR(S)  : Kenji Nishioka, John S. McMurray, B. Montgomery Pettitt and Fahad Al-Obeidi It is certified that error appears in the above-identified patent and that said Letters Patent is hereby corrected as shown below:

<u>Column 8,</u>
Line 43, delete "cycl" and insert -- cyclo --

This certificate supersedes Certificate of Correction issued October 16, 2001.

Signed and Sealed this

Twenty-fifth Day of June, 2002

*Attest:*

*Attesting Officer*

JAMES E. ROGAN
*Director of the United States Patent and Trademark Office*